United States Patent [19]

Lobunez et al.

[11] 3,981,939

[45] Sept. 21, 1976

[54] HYDROCHLORINATION OF VINYLIDENE CHLORIDE TO PRODUCE METHYL CHLOROFORM

[75] Inventors: Walter Lobunez, Princeton; Sidney Berkowitz, Highland Park, both of N.J.

[73] Assignee: FMC Corporation, Philadelphia, Pa.

[22] Filed: June 13, 1975

[21] Appl. No.: 586,782

Related U.S. Application Data

[63] Continuation-in-part of Ser. No. 886,071, Dec. 18, 1969, abandoned.

[52] U.S. Cl. .............................. 260/658 R; 260/663
[51] Int. Cl.² ................... C07C 17/04; C07C 17/08
[58] Field of Search ..................... 260/658 R, 663

[56] References Cited
UNITED STATES PATENTS

| | | | |
|---|---|---|---|
| 2,209,000 | 7/1940 | Nutting et al. | 260/658 R |
| 2,945,897 | 7/1960 | Eisenlohr | 260/663 |
| 3,707,574 | 12/1972 | Stephan et al. | 260/658 R |
| 3,760,015 | 7/1973 | Berkowitz | 260/658 R |
| 3,776,969 | 12/1973 | Lobunez | 260/658 R |
| 3,919,337 | 11/1975 | Gordon et al. | 260/658 R |

*Primary Examiner*—Daniel E. Wyman
*Assistant Examiner*—Thomas A. Waltz

[57] ABSTRACT

Vinylidene chloride is hydrochlorinated to methyl chloroform by passing the reactants into a suspension of a Friedel-Crafts carrier, preferably ferric chloride, suspended in a liquid medium selected from the group consisting of 1,1,2-trichloroethane and perchloroethylene.

4 Claims, 1 Drawing Figure

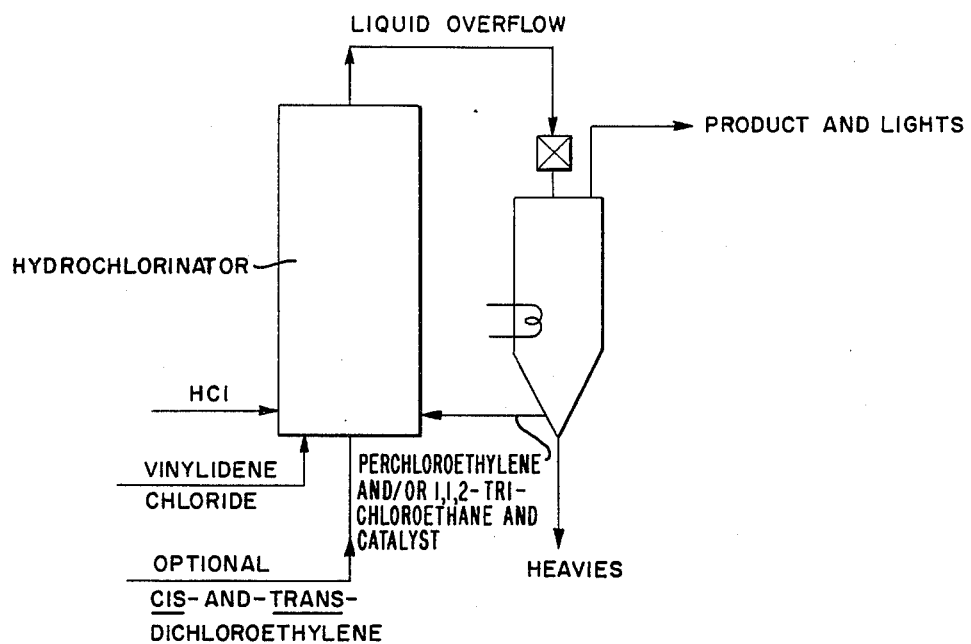

HYDROCHLORINATION OF VINYLIDENE CHLORIDE TO PRODUCE METHYL CHLOROFORM

CROSS-REFERENCE TO RELATED APPLICATIONS

This application is a continuation-in-part of U.S. Ser. No. 886,071, filed Dec. 18, 1969, now abandoned.

FIELD OF THE INVENTION

This invention relates to the production of methyl chloroform by the reaction of vinylidene chloride and hydrogen chloride.

RELATED APPLICATIONS

This application is related to the Berkowitz application entitled "Production of Vinylidene Chloride and Methyl Chloroform", Ser. No. 886,378, filed Dec. 18, 1969 (now U.S. Pat. No. 3,760,015, issued Sept. 18, 1973), and the Lobunez application entitled "Production of Methyl Chloroform From Ethylene and Chlorine", Ser. No. 886,070, filed Dec. 18, 1969 (now U.S. Pat. No. 3,776,969, issued Dec. 4, 1973).

BACKGROUND OF THE INVENTION

The production of methyl chloroform — 1,1,1-trichloroethane — by the hydrochlorination of vinylidene chloride-1,1-dichloroethylene is well known. The basic process was described many years ago in the Nutting et al U.S. Pat. No. 2,209,000. In that patent, vinylidene chloride and hydrogen chloride are reacted under pressure in the presence of a Friedel-Crafts catalyst such as ferric chloride, maintaining the reaction at below 75°C. The process is expensive to carry out commercially, since it is a pressure reaction. More recent workers — see Vogt U.S. Pat. No. 3,065,280 and Dynamit Nobel German Pat. No. 1,231,226 — have carried out the process at ambient pressures by suspending the catalyst in methyl chloroform, and passing the reactants into the mixture. The process works well, but the conversions obtained are rather poor, and catalyst activity falls off rapidly.

OBJECTS OF THE INVENTION

It is the principal object of the present invention to improve the hydrochlorination of vinylidene chloride to methyl chloroform, to get much improved conversion and catalyst lift as compared to prior art procedures.

STATEMENT OF THE INVENTION

We have discovered that these objects may be attained by conducting the hydrochlorination of vinylidene chloride in an anhydrous suspension of a hydrochlorination catalyst such as ferric chloride, in either 1,1,2-trichloroethane or perchloroethylene carrier, maintaining the temperature below 75°C. Surprisingly, conversion rates ae sharply increased over the same process in methyl chloroform, and catalyst life is extended to a very marked degree.

DRAWING

The attached drawing is a flow sheet of the process of the invention.

DETAILED DESCRIPTION OF THE INVENTION

In practicing the invention, vinylidene chloride is reacted with hydrogen chloride at a temperature below 75°C, and preferably at about 25°–55°C, in an anhydrous suspension of a hydrochlorination catalyst such as ferric chloride or other Friedel-Crafts catalyst, in either or both perchloroethylene or 1,1,2-trichloroethane. The reactants are fed into the suspension, and the reaction simply proceeds. When the process is run batch-wise, product must not be permitted to build up to the point where it is the major constituent of the reaction mixture. Most advantageously, the process is run continuously, as shown in the attached flow sheet.

The reactants are fed into the bottom of a hydrochlorinating column filled with a suspension of ferric chloride, or other catalyst, in perchloroethylene or 1,1,2-trichloroethane. The catalyst concentration is not critical; from a few tenths to a few percent of catalyst, based on total weight, will drive the reaction forward at a good rate. Optimum results are obtained at from about 1 to 5% of catalyst. The essential reactants are vinylidene chloride and HCl. Optionally, mixtures of HCl, vinylidene chloride and cis- and trans-dichloroethylene, obtained by pyrolyzing 1,1,2-trichloroethane at 300°–500°C in the presence of sodium chloride crystals, in accordance with the Berkowitz U.S. Pat. No. 3,760,015 may be used.

The liquid is maintained at under 75°C, preferably between about 25° and 55°C, at autogenous pressure, and the reactants are fed into the bottom of the reactor at a rate to insure sufficient hold time for the reaction to proceed to the desired degree of completion. We find a desirable addition rate of organics to be hydrochlorinated to be from 5 to 20% of the liquid volume per hour. The liquid is permitted to overflow to a still, where the lights and product are collected overhead, and the catalyst, suspended in the heavier perchloroethylene and/or 1,1,2-trichloroethane, is returned to the hydrochlorinator; this return of the carrier and catalyst, along with the continuous feeding of fresh reactants maintains the reaction body at a reasonably steady volume.

The superiority of these high boilers over methyl chloroform as a medium is indeed surprising. In the laboratory, this superiority can be demonstrated in the following way:

The reaction system used in this work consisted of a glass-tube reactor (1.25 inches i.d.) sealed at the bottom and having an overflow outlet at the upper end. The length from the bottom of the reactor to the overflow tube was 29 inches. The reactants were introduced into the bottom part of the reactor through a Monel tube (0.25 inch o.d.) inserted through the top of the reactor and extending close to its bottom. This tube served also as a shaft for the mixing blades made of Teflon and was connected at its upper end to a vibromixer. The amounts of gaseous reactants introduced into the reactor were measured with flowmeters, and of liquid reactants with a balance. The reaction temperature was measured with thermocouples placed in a glass thermowell inserted in the reactor and was regulated by use of a tubular furnace and air-cooling. The reaction products emerged through a tube at the upper end of reactor, passed through a heated gas-sampling tube and an alkali or water trap for collecting HCl and were vented. There was also a side tube for sampling the liquid in the upper part of the reactor. HCl was determined volumetrically and the rest of products with a gas chromatograph. Before starting the reaction, the reactor was filled with 500 ml. of a diluent to which 16 g. of anhydrous FeCl₃ was added. The diluents were distilled before beginning of the experiments. The results of two series of experiments are presented below:

Table 1

| Diluent | Methyl chloroform | | |
|---|---|---|---|
| Experiment No. | A | B | C |
| Reactants (mmol/minute): | | | |
| $CH_2=CCl_2$ | 11.4 | 10.8 | 11.4 |
| HCl | 17.7 | 17.7 | 17.7 |
| $N_2$ | 4.8 | 4.9 | 4.9 |
| Reaction temperature, °C | 33 | 56 | 55 |
| % of the theoretical amount of HCl | 155 | 164 | 155 |
| Sampling time (in minutes since start of reaction) | 12 | 54 | 88 |
| % Vinylidene chloride utilized | 44 | 37 | 21 |

Table 2

| Diluent | 1,1,2-Tri-chloroethane | | | Perchloro-ethylene | |
|---|---|---|---|---|---|
| Experiment No. | 1 | 2 | 3 | 4 | 5 |
| Reactants (mmol/minute): | | | | | |
| $CH_2=CCl_2$ | 10.9 | 13.4 | 9.4 | 9.8 | 13.1 |
| HCl | 15.6 | 20.0 | 14.0 | 17.2 | 14.6 |
| $N_2$ | 4.7 | 6.8 | 4.8 | — | — |
| Reaction temperature, °C | 54 | 46 | 44 | 41 | 31–34 |
| % of the theoretical amount of HCl | 143 | 150 | 158 | 176 | 112 |
| Sampling time (in minutes since start of reaction) | 60 | 125 | 35 | 120 | 100 |
| % Vinylidene chloride utilized | 91.5 | 93.7 | 98.0 | 96 | 92 |

It will be noted that in the prior art procedure, conversions are all under 50% at the rates selected, and that conversions fell off to less than half the original after 88 minutes. In the case of the suspending media of this invention, conversions of over 90% were obtained, with substantially no falling off in activity after 2 hours.

Obviously, examples can be multiplied indefinitely without departing from the scope of the invention as defined in the claims.

What is claimed is:

1. The method of hydrochlorinating vinylidene chloride to produce methyl chloroform, which comprises continuously introducing into the reactor vinylidene chloride and hydrogen chloride concurrently into a liquid body of an anhydrous carrier, of the group consisting of 1,1,2-trichloroethane and perchloroethylene, containing suspended in it a hydrochlorination catalyst, at a temperature below 75°C, and maintaining the reactants in contact with the liquid body until a major portion of the vinylidene chloride has been converted to methyl chloroform, and continuously withdrawing from said reactor a mixture including methyl chloroform, catalyst and carrier, separating methyl chloroform from catalyst and carrier and returning catalyst and carrier to the liquid body to maintain the liquid body at a steady volume.

2. The method of claim 1, in which the catalyst is ferric chloride.

3. The method of claim 1, in which the temperature is 25°–55°C.

4. The method of claim 1, in which the reaction is carried out continuously by feeding the reactants to a long column of the carrier containing the catalyst, and overflowing the suspension from near the top of the column.

* * * * *